United States Patent [19]

Houbiers

[11] Patent Number: 4,585,595
[45] Date of Patent: Apr. 29, 1986

[54] OPTICALLY ACTIVE DERIVATIVES OF MERCAPTOISOBUTYRIC ACID AND METHODS OF PREPARATION THEREOF

[75] Inventor: Joannes P. M. Houbiers, Tegelen, Netherlands

[73] Assignee: Océ-Andeno B.V., Venlo, Netherlands

[21] Appl. No.: 71,934

[22] Filed: Sep. 4, 1979

[30] Foreign Application Priority Data

Sep. 7, 1978 [NL] Netherlands ............... 7809121

[51] Int. Cl.$^4$ ..................................... C07C 153/023
[52] U.S. Cl. ................................... 558/255; 548/572
[58] Field of Search ............................ 260/455 R

[56] References Cited

U.S. PATENT DOCUMENTS

| | | | |
|---|---|---|---|
| 2,408,095 | 9/1946 | Peppel | 260/455 R |
| 3,636,033 | 1/1972 | Kleiner | 260/455 R |
| 4,105,776 | 8/1978 | Ondetti et al. | 546/188 |
| 4,224,457 | 9/1980 | Iwao et al. | 562/401 |

OTHER PUBLICATIONS

Cushman et al., Biochemistry, vol. 16, No. 25, pp. 5484–5490 (1977).
Karrer—Organic Chemistry, 2nd English Edition, pp. 92–102 (1946), Elsevier Publg. Co., N.Y.
Eliel, Stereochemistry of Carbon Compounds, pp. 48–53, McGraw-Hill, Inc., 1962, New York.
Radke et al., JACS, 76, (1954), pp. 2801–2803.
Wilen, Resolving Agents in Organic Chem., Wiley, N.Y., 1971.
Overberger et al., Jour. Am. Chem. Soc., 90:13, Jun. 19, 1968.
Scopes et al., J. Chem. Soc., C 1971, (9), 1671–1676.
Chem. Abs., 53:1321c, 1959.
Chem. Abs., 67:11045c, 1967.
Chem. Abs., 65:2287c, 1966.
Chem. Berichte, Johrg. 99, pp. 1528–1531.
Chem. Abs., 69:26609e, 1968.

Primary Examiner—Henry R. Jiles
Assistant Examiner—Robert C. Whittenbaugh
Attorney, Agent, or Firm—Albert C. Johnston

[57] ABSTRACT

Optically active compounds of formula

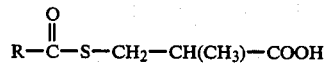

in which R is either a $H_3C-$, $(CH_3)_3C-$, $(CH_3)_3CO-$, $C_6H_5CH_2O-$, $C_6H_5-$, $o-NO_2C_6H_4-$, $p-NO_2C_6H_4-$ or a $p-CH_3C_6H_4-$group, or salts or lower alkyl esters thereof. The compounds are prepared by the following sequence of reaction steps:

(a) there is started from a racemic mixture of a compound according to said formula in which R=a $C_6H_5$ group,
(b) cinchonidine, D(—)-2-aminobutanol-1 or a derivative thereof is added to this compound as resolving agent,
(c) the D(—)-salt of the resolving agent formed is crystallized out and isolated,
(d) if necessary, this salt is further purified of the L-isomer by recrystallization,
(e) the pure D(—)-salt is hydrolysed in order to remove the resolving agent,
(f) the D(—)-S-benzoyl-β-mercaptoisobutyric acid thus liberated is won and, if necessary, purified, and
(g) if desired, the $C_6H_5$ group is replaced, in a way known per se, by one of the other possible groups indicated above for R.

7 Claims, No Drawings

OPTICALLY ACTIVE DERIVATIVES OF MERCAPTOISOBUTYRIC ACID AND METHODS OF PREPARATION THEREOF

The invention relates to new, optically active compounds according to the general Formula 1 of the formula sheet, or to salts or esters of these compounds, in which R is either a $H_3C-$, $(CH_3)_3C-$, $(CH_3)_3CO-$, $C_6H_5CH_2-O-$, $C_6H_5-$, $o-NO_2C_6H_4-$, $p-NO_2C_6H_4-$ or a $p-CH_3C_6H_4-$ group. As appears from Formula 1, the asterisked carbon atom is asymmetric, so that the compounds, briefly referred to as derivatives of β-mercaptoisobutyric acid, can be present in the D—, L— and DL—form. Though various compounds according to the invention in their racemic form are new compounds, claims are presented only for their optically active forms and, in view of the possible application of these compounds (to which will be referred later on) for the D-isomer, which is levorotatory, in particular. The invention does relate, of course, to the salts and esters of the compounds according to the invention, which can both be easily prepared in a way known per se. In this connection, ammonium salts, alkaline (earth) metal salts such as the Na—, K—, Ca—, Ba— and Mg—salt, and simple esters such as the lower alkyl esters, may particularly be considered.

The invention also relates to a process for the preparation of these new derivatives of β-mercaptoisobutyric acid, which process is characterized in that:
(a) there is started from a racemic mixture of a compound according to the general Formula 1 of the formula sheet, in which R is a $C_6H_5$ group,
(b) to this compound cinchonidine, D(—)-2-aminobutanol-1 or a derivative thereof is added as resolving agent,
(c) the D(—)-salt of the resolving agent formed is crystallized out and isolated,
(d) if necessary, this salt is further purified of the L-isomer by recrystallization,
(e) the pure D(—)-salt is hydrolysed in order to remove the resolving agent,
(f) the D(—)-S-benzoyl-β-mercaptoisobutyric acid thus liberated is won and, if necessary, purified, and
(g) if desired, the $C_6H_5$-group is replaced, in a way known per se, by one of the other possible groups indicated above for R.

Due to the fact that this separation process is realized far best with a compound according to Formula 1, in which $R=C_6H_5$, and the process is thus limited accordingly, it may be clear that this compound, but then in its optically active form, is preferred. An additional advantage is that the reaction step (g) can be omitted.

As is well known, in separating a racemic mixture, efficiency is chiefly determined by a specific crystallization of the desired salt formed from the racemic compound and the resolving agent. Therefore, it is plain that the choice of the solvent system to be applied may be of great importance.

It has appeared that in the present case, where cinchonidine is used as a resolving agent, the above-mentioned steps (a) to (d) inclusive can be carried out in a lower boiling aliphatic ketone. By 'lower boiling' is meant here: having a boiling point lower than approximately 125° C. Examples of such lower boiling aliphatic ketones are: acetone, methylethyl ketone, diethyl ketone, methyl-n-propyl ketone, methyl-t-butyl ketone and hexanone, of which acetone is preferred.

If, on the other hand, D(—)-2-aminobutanol-1, for example, was used as a resolving agent the choice of the solvent for the reaction steps (a) to (d) inclusive proved to be not quite specific. Examples of useful solvents are 1,2-dichloroethane, ethyl acetate and toluene, of which toluene is preferred.

In addition to the resolving agents referred to above, which are preferred, some more optically active bases proved to be effective, although to a lesser degree. Examples of such bases are α-naphthylethylamine and ephedrine. The use of other optically active bases, such as quinine and dehydroabiethylamine, resulted in crystallization of the undesired isomer.

The compounds according to the invention can be used as starting compounds for the preparation of 1-(3-mercapto-2-D-methylpropanoyl)-L-proline and its derivatives, which are biologically active compounds with interesting pharmaceutical properties, such as their lowering effect on certain forms of hypertension.

The preparation of the racemic mixture of the compounds can be effected with the aid of reaction methods which are usual in organic chemistry.

The following is an example of how DL-S-benzoyl-β-mercaptoisobutyric acid was prepared by the routes I and II indicated on the formula sheet.

PREPARATION OF DL-S-BENZOYL-β-MERCAPTOISOBUTYRIC ACID

(A) By Route I

A mixture of 1.00 mol of methacrylic acid and 1.05 mol of thiobenzoic acid was stirred for 1½ to 2 hours at a temperature between 95° and 100° C. and, after cooling to approximately 40° C., poured out in 500 ml of hexane. During prolonged cooling to about 20° C. the reaction product crystallized out. This product was isolated, washed three times with 50 ml of hexane in each case and dried in the air. The yield of DL-S-benzoyl-β-mercaptoisobutyric acid was 92%; melting point: between 59.8° and 61° C.

(B) By Route II

With stirring, 1 mol of methacrylic acid was added to 1.4 mol of fresh-distilled thioacetic acid being kept under $N_2$ atmosphere. To the extent it was still necessary to do so in view of the heat liberated in course of the reaction, the reaction mixture was heated slowly to approximately 95° C. (reflux) and, subsequently, maintained at this temperature for 1 to 2 hours. After removing the excess thioacetic acid by distillation at atmospheric pressure, crude DL-S-acetyl-β-mercaptoisobutyric acid was obtained by the process of vacuum distillation (about 135° C. at 4 mm Hg). To purify this crude product, it was poured out in 200 ml of hexane and the product crystallized out was filtered off and dried in the air. The yield was 70%; melting point: about 39° C. (literature: 40°–40.5° C.; Chemical Abstracts 38, 3616).

For the purpose of alkaline deacetylation, 0.1 mol of the pure DL-S-acetyl-β-mercaptoisobutyric acid obtained above was added at room temperature to 0.3 mol of NaOH dissolved in 90 ml of water, which was kept under $N_2$ atmosphere. After stirring the mixture for approximately 3 hours it was cooled to about 0° C., whereupon 0.1 mol of benzoyl chloride was added. After additional stirring for about 2 hours at a temperature between 0° and 5° C. the DL-S-benzoyl-β-mercaptoisobutyric acid was obtained by acidifying the reaction mixture with hydrochloric acid up to pH≦2 and extracting it by means of 1,2-dichloroethane. The crude product was purified by stirring up in hexane. The crystalline product was filtered off and dried in the air. The yield was 80%; melting point: about 60° C. If the removal of the excess thioacetic acid was followed immediately by alkaline hydrolysis and benzoylation, the yield was 71.4%.

According to the invention the DL-S-benzoyl-β-mercaptoisobutyric acid prepared in the way described above can be separated into its optical antipodes by means of the following steps:
(1) salification with the resolving agent
(2) recrystallisation of the salt thus formed
(3) removal of the resolving agent, as a result of which the D(—)-isomeris liberated
(4) recrystallisation, if necessary, of the liberated D(—)-isomer.

The following examples may serve to illustrate the process according to the invention.

1. SEPARATION OF DL-S-BENZOYL-β-MERCAPTOISOBUTYRIC ACID BY MEANS OF CINCHONIDINE

(1) Salification with Cinchonidine 294.5 g (=1 mol) of cinchonidine were added to 5,100 ml of acetone and the mixture was heated to 45°–50° C. To this mixture 224 g (=1 mol) of DL-S-benzoyl-β-mercaptoisobutyric acid were added. The solution obtained was additionally heated to approximately 60° C. (reflux temperature) and maintained at that temperature for about half an hour. The solution was then cooled, with stirring, to about 20° C. The stirring at room temperature was continued overnight and, the morning after, the precipitated cinchonidine salt of D(—)-S-benzoyl-β-mercaptoisobutyric acid was filtered off and washed three times with acetone. The yield was 233 g=45%.

(2) Recrystallisation of the Cinchonidine Salt

The 233 g of cinchonidine salt obtained above were added to 2,300 ml of acetone, after which the temperature of the mixture was raised to approximately 60° C. (reflux temperature). As the solution was not clear, it was filtered. The filtrate was cooled to about 20° C. and allowed to stand one night. The morning after, the salt was filtered off and washed three times with 50 ml-portions of acetone. The yield was 151.5 g=65%. This purification step had to be repeated twice before the salt crystallized out was sufficiently pure, id est, before it possessed an $[\alpha]_D \geq -96°$ (1% in 96% ethanol).

(3) Liberation of the D(—)-isomer from the Cinchonidine Salt

With stirring, 260 ml of hydrochloric acid, 800 ml of 1,2-dichloroethane and 520 g of the cinchonidine D(—)-salt prepared according to (1) and (2) were added to 2,300 ml of water. The mixture was stirred for half an hour. The organic layer was separated, the water layer was extracted twice with 200 ml-portions of dichloroethane and the organic layers were combined to form one organic phase. This organic phase was dried by means of magnesium sulphate. After evaporation of the solvent 200 g (=approximately 90%) of crude D(—)-S-benzoyl-β-mercaptoisobutyric acid with an $[\alpha]_D = -40°$ (1% in 96% ethanol) remained.

(4) Recrystallisation of the Liberated D(—)-isomer 198 g of the crude product obtained by the process (3) were added to 1,300 ml of cyclohexane, after which the mixture was heated until all the salt had dissolved (about 70° C.). The solution was filtrated by passing it through a pre-heated filter and the filter was washed three times with warm cyclohexane (25 ml-portions). The filtrate was cooled slowly to approximately 10° C., after which the mixture was stirred at this temperature for about 1 hour. The precipitated D(—)-S-benzoyl-β-mercaptoisobutyric acid was filtered off and washed three times with 50 mo-portions of cyclohexane. The yield was 167 g=85%; melting point: 67.6°–68.7° C.; $[\alpha]_D = -45.1°$ (1% in 96% ethanol).

In connection with the yields mentioned above it should be noted that from the various mother liquors and filtrates there resulted a recovery amounting to 35% of the racemic acid started from. As this acid can be reused, this means that the reaction steps referred to under (1) and (2) lead in fact to higher yields. Moreover, the cinchonidine could be recovered quantitatively.

2. SEPARATION OF DL-S-BENZOYL-β-MERCAPTOISOBUTYRIC ACID BY MEANS OF D(—)-2-AMINOBUTANOL-1

(1) Salification with D(—)-2-aminobutanol-1

With stirring, a solution of 224 g of DL-S-benzoyl-β-mercaptoisobutyric acid was prepared at room temperature in 3,000 ml of toluene. Stirring all the time, 89.2 g of D(—)-2-aminobutanol-1 were added to the solution, the temperature rising to about 30° C. Some seed crystals were added, after which the mixture was stirred slowly for another 4 hours in order to allow the desired salt to crystallize out completely. Meanwhile, the temperature had dropped to approximately 20° C. The salt was filtered off and washed three times with 50 ml-portions of toluene. After drying, the yield was 114 g=about 36&, $[\alpha]_D = -31°$ (1% in 96% ethanol).

(2) Recrystallization of the 2-aminobutanol-1-salt 110 g of the 114 g of salt obtained above were added to 1,100 ml of toluene, and the temperature of the mixture was increased to between 70° and 75° C. in order to dissolve the salt completely. The solution was then cooled slowly. Some seed crystals were added at a temperature of about 60° C. The crystallization process started at a temperature between 55° and 58° C. The mixture was then further cooled to approximately 20° C., after which the salt was filtered off and washed three times with 45 ml-portions of toluene. After drying, the yield was 97.5 g=about 88%; $[\alpha]_D = -34.5°$ (1% in 96% ethanol).

(3) Liberation of the D(—)-isomer from the 2-aminobutanol-1-salt

With stirring, 50 ml of hydrochloric acid, 200 ml of ether and the 97.5 g of 2-aminobutanol-1-salt mentioned above were added to 150 ml of water. The mixture was stirred for 15 minutes. The organic layer was separated, the water layer was extracted twice with ether and the organic layers were combined to form one organic phase. This organic phase was dried with magnesium sulphate and evaporated. The yield was 68.2 g=about 97.5%; $[\alpha]_D = -43°$ (1% in 96% ethanol). In this case the purity of the D(—)-S-benzoyl-β-mercaptoisobutyric acid sufficed to render recrystallization (the 4th reaction step) superfluous.

Besides D(—)-2-aminobutanol-1 itself, a derivative thereof, such as optically active 2-benzylaminobutanol-1, can be used as a resolving agent.

The undesirable L-isomer could be returned to the racemic starting material by racemization, the process according to the invention thus being made more attractive from the economic point of view. This can be done, for example, by heating the acid chloride of the L-isomer followed by hydrolysis and isolation of the racemic acid.

For the preparation of one of the remaining seven compounds referred to in the opening paragraph of this application, there is started from the pure D(—)-S-benzoyl-β-mercaptoisobutyric acid obtained above, in which the benzoyl group is replaced by one of the other protective groups mentioned in the said opening paragraph. This can be realized by debenzoylating the benzoyl compound in a way known per se, and acylating it again with the desired group. An example of such a deacylating process followed by acylating with the desired group is represented in route II described above, in which the acetyl group being originally present was replaced by a benzoyl group. Another example is the replacement, described hereinafter, of a benzoyl group by a pivaloyl group:

(a) Methanolysis of D(—)-S-benzoyl-β-mercaptoisobutyric Acid 22.4 g (0.10 mol) of S-benzoyl-β-mercaptoisobutyric acid having an $[\alpha]_D^{20} = -45°$ (1% in 96% ethanol) were dissolved in 150 ml of dry methanol. The solution was cooled to 0° C. and, meanwhile, the air above the solution was replaced by nitrogen. An amount of 13.5 g (0.25 mol) of sodium methoxide was added in doses at 0° C. The mixture was stirred for 1.5 hours at 0° C. under nitrogen atmosphere. When the debenzoylation was complete (checked by TLC using silica gel; elution agent: dichloroethane/acetone/formic acid in the ratio of 18:2:0.25) 9.01 g (0.15 mole or 8.59 ml) of glacial acetic acid were added to the mixture. The methanol was largely removed by distilling it under reduced pressure and 200 ml of water were added to the residue. The pH of the resulting solution was 8 or 9. To remove the methyl benzoate the solution was extracted 3 times with 50 ml-portions of methylene chloride. Then, the remainder of methanol was removed under reduced pressure from the water layer, which was further acidified to pH $\leq 1$ by the addition of concentrated hydrochlorid acid. Extraction with methylene chloride (three 50 ml-portions), washing the combined organic phases with a saturated solution of sodium chloride (two 25 ml-portions) and drying by means of magnesium sulphate yielded, after removal of the solvent, 11.4 g (95%) β-mercaptoisobutyric acid ($[\alpha]_D^{20} - 23.9°$; 1% in 96% ethanol) in the form of a colourless clear liquid.

(b) Pivaloylation of β-mercaptoisobutyric Acid

Under nitrogen atmosphere 8.1 g (0.20 mol) of sodium hydroxide were dissolved in 61 ml of water. Subsequently, 12.0 g (0.10 mol) of β-mercaptoisobutyric acid ($[\alpha]_D^{20} - 23.9°$; 1% in 96% ethanol) were dissolved at a temperature of 0° C. and at this temperature, 12.3 g of pivaloyl chloride were added in an hour's time. The mixture was stirred until the pivaloylation process had been completed (checked by TLC using silica gel; elution agent: dichloroethane/acetone/formic acid in the ratio of 18:2:0.25).

The process proved to take approximately one hour. The reaction mixture was acidified, using concentrated hydrochloric acid, to pH <3 and extracted with dichloroethane (three 100 ml-portions). The combined organic phases were washed with small quantities of a saturated solution of sodium chloride, dried by means of magnesium sulphate and evaporated under reduced pressure. A yield amounting to 20.3 g of crude product was obtained which, after heating for the purpose of rendering it oily, was poured out into 1 liter of n-hexane. The solution was cooled to 0° C. With stirring, seed crystals were added. The crystallized pivaloyl compound was isolated on a Büchner funnel, washed with hexane and dried. A yield of 19.4 g (=95%) of D-(—)-S-pivaloyl-β-mercaptoisobutyric acid, melting point 51°-52° C.; $[\alpha]_D = -44.7°$ (1% in 96% ethanol) was obtained.

Instead of using an acid chloride the acylating process can also be carried out with an anhydride.

Thus, D(—)-S-acetyl-β-mercaptoisobutyric acid was obtained by adding 12.0 g of acetic anhydride to 12 g of the D(—)-β-mercaptoisobutyric acid prepared according to process (a), which, working according to process (b) yielded, after a reaction time of one hour, 16 g of a colourless oil.

Recrystallization from n-hexane at —30° C. resulted in a yield of 14.4 g (=89%) having $n_D^{20} = 1.4886$ and $[\alpha]_D = -46.6°$ (1% in 96% ethanol).

The table to follow exhibits the yields and physical constants for the various compounds of the invention (Formula 1 of the formula sheet).

| | R | yield in % | melting point in °C. | $n_D^{20}$ | $[\alpha]_D^{22}$ 1% in 96% ethanol | solvent |
|---|---|---|---|---|---|---|
| 1. | H₃C | 89 | — | 1.4886 | —46.6 | n-hexane |
| 2. | (CH₃)₃C | 95 | 51–52 | — | —44.7 | " |
| 3. | (CH₃)₃CO | 85 | 40–41 | — | —43.0 | " |
| 4. | C₆H₅CH₂O | 95 | 57–57.5 | — | —40.3 | " |
| 5. | C₆H₅ | 92 | 66–67 | — | —44 | " |
| 6. | o-NO₂C₆H₄ | 93 | 40–41[1] | — | —31.1 | benzene |
| 7. | p-NO₂C₆H₄ | 89 | 122–123 | — | —31.4 | " |
| 8. | p-CH₃C₆H₄ | 93 | 70–71 | — | —40.9 | n-hexane |
| | H | 95 | — | — | —23.9 | |

[1] a trace of benzene was present

All products were spectroscopically pure (NMR and IR). The retention of optical activity is proved, i.a., by the fact that debenzoylation and rebenzoylation of the starting compound D-(—)-S-benzoyl- 62 -mertcaptoisobutyric acid resulted in a product having almost the same $[\alpha]_D$ as the starting compound.

I claim:

1. Process for preparing in isolated, substantially pure form the D (-) stereoisomer of a compound of the formula

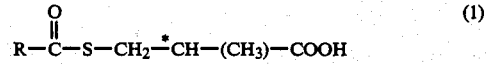

in which R is a H₃C—, (CH₃)₃C—,(CH₃)₃CO—, C₆H₅CH₂O—,C₆H₅,o-NO₂C₆H₄—, p-NO₂C₆H₄—, or p-CH₃C₆H₄—group, or a salt or a lower alkyl ester of such compound, characterized in that (a) there is started from a racemic mixture of a compound of said formula (1) in which R=a $C_6H_5$ group,
(b) either (1) said mixture is dissolved in acetone and cinchonidine is added to it as resolving agent or (2) said mixture is dissolved in toluene and D(—)-2-aminobutanol-1 or a derivative thereof is added to it as resolving agent,
(c) the formed D(—)- salt of the resolving agent is crystallized out and isolated,
(d) if necessary, this salt is further purified of the L-isomer by recrystallization,
(e) the pure D(—)- salt is subjected to an acid hydrolysis process, in order to remove the resolving agent,
(f) the D(—)-S-benzoyl-β-mercaptoisobutyric acid thus liberated is won and, if necessary, purified.

2. Process according to claim 1, characterized in that the resolution is carried out with cinchonidine and acetone.

3. Process according to claim 1, characterized in that the resolution is carried out with D(—)-2-aminobutanol-1 and toluene.

4. The compound D(—)-3-t-butyloxythio-isobutyric acid.

5. The compound D(—)-3-benzyloxythio-isobutyric acid.

6. Process according to claim 1, and replacing the $C_6H_5$ group of the liberated acid by one of the other groups specified for R in said formula (1).

7. Process according to claim 1 or 6, and converting said acid of D(—) stereoisomeric form to a salt or a lower alkyl ester thereof.

* * * * *